US010034739B2

(12) United States Patent
Florescu

(10) Patent No.: US 10,034,739 B2
(45) Date of Patent: Jul. 31, 2018

(54) STENT TO ASSIST IN ARTERIOVENOUS FISTULA FORMATION

(71) Applicant: BOARD OF REGENTS OF THE UNIVERSITY OF NEBRASKA, Lincoln, NE (US)

(72) Inventor: Marius C. Florescu, Omaha, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 0 days.

(21) Appl. No.: 15/438,210

(22) Filed: Feb. 21, 2017

(65) Prior Publication Data
US 2017/0156845 A1 Jun. 8, 2017

Related U.S. Application Data

(62) Division of application No. 14/409,304, filed as application No. PCT/US2013/046370 on Jun. 18, 2013.
(Continued)

(51) Int. Cl.
  *A61F 2/06* (2013.01)
  *A61M 1/36* (2006.01)
  (Continued)

(52) U.S. Cl.
  CPC ............... *A61F 2/06* (2013.01); *A61B 17/11* (2013.01); *A61F 2/064* (2013.01); *A61F 2/915* (2013.01);
  (Continued)

(58) Field of Classification Search
  CPC ...................................................... A61F 2/064
  See application file for complete search history.

(56) References Cited

U.S. PATENT DOCUMENTS 3,882,862 A 5/1975 Berend
4,553,545 A 11/1985 Maass et al.
(Continued)

OTHER PUBLICATIONS

Akoh; Prosthetic arteriovenous grafts for hemodialysis; J. Vasc. Access; 10(3); pp. 137-147; Jul.-Sep. 2009.
(Continued)

*Primary Examiner* — Christopher D Prone
*Assistant Examiner* — Suba Ganesan
(74) *Attorney, Agent, or Firm* — Suiter Swantz pc llo

(57) ABSTRACT

There is described an arteriovenous fistula stent, having a tubular body comprising a series of sinusoidal shaped struts along the length of the tubular body. A plurality of curvilinear connectors extend between and are attached to adjacent struts wherein a first end of a connector is attached to a distal face of a proximal strut apex and a second end of a connector is attached to a proximal face of a distal strut apex. A pair of unconnected strut apexes are between pairs of connected apexes. When the tubular body is in a stowed configuration a proximal aperture and a distal aperture are circular and when the tubular body is in a deployed configuration the distal aperture is oblong or ovoid. There is also described a method for inserting a stent for use in creation of an arteriovenous fistula by identifying a candidate artery and a candidate vein and dissecting the candidate vein. Next, inserting a stent into the vein and creating a breach in the candidate artery at a desired angle and location. Next, introducing the stent and vein into the candidate artery and forming the stent into a curvature angle selected to minimize turbulent blood flow in an anastomosis formed by the vein and the artery. Optionally, there is a step of fastening a distal portion of the stent to the artery.

12 Claims, 13 Drawing Sheets

Related U.S. Application Data

(60) Provisional application No. 61/661,133, filed on Jun. 18, 2012.

(51) Int. Cl.
| | | |
|---|---|---|
| *A61M 25/10* | (2013.01) | |
| *A61F 2/915* | (2013.01) | |
| *A61F 2/958* | (2013.01) | |
| *A61B 17/11* | (2006.01) | |

(52) U.S. Cl.
CPC .......... *A61F 2/958* (2013.01); *A61M 1/3655* (2013.01); *A61M 25/104* (2013.01); *A61B 2017/1107* (2013.01); *A61B 2017/1135* (2013.01); *A61F 2002/91558* (2013.01); *A61F 2220/0016* (2013.01)

(56) References Cited

U.S. PATENT DOCUMENTS

| | | | |
|---|---|---|---|
| 4,813,925 | A | 3/1989 | Anderson, Jr. et al. |
| 5,372,600 | A | 12/1994 | Beyar et al. |
| 5,476,505 | A | 12/1995 | Limon |
| 5,676,685 | A | 10/1997 | Razavi |
| 5,824,053 | A | 10/1998 | Khosravi et al. |
| 5,935,145 | A | 8/1999 | Villar et al. |
| 6,746,464 | B1 | 6/2004 | Makower |
| 6,872,218 | B2 | 3/2005 | Ferrera et al. |
| 6,926,724 | B1 | 8/2005 | Chu |
| 6,974,473 | B2 | 12/2005 | Barclay et al. |
| 7,691,140 | B2 | 4/2010 | Bates et al. |
| 7,828,814 | B2 | 11/2010 | Brenneman et al. |
| 7,867,272 | B2 | 1/2011 | Niermann |
| 8,062,328 | B2 | 11/2011 | Hallisey |
| 8,535,345 | B2 | 9/2013 | Desai et al. |
| 2005/0228472 | A1 | 10/2005 | Case et al. |
| 2006/0193892 | A1 | 8/2006 | Furst et al. |
| 2006/0241675 | A1 | 10/2006 | Johnson et al. |
| 2007/0088482 | A1 | 4/2007 | Mailer |
| 2007/0100437 | A1 | 5/2007 | Welborn et al. |
| 2008/0200979 | A1 | 8/2008 | Dieck et al. |
| 2008/0306580 | A1 | 12/2008 | Jenson et al. |
| 2009/0054966 | A1 | 2/2009 | Rudakov et al. |
| 2010/0010613 | A1 | 1/2010 | Dorn |
| 2010/0100170 | A1 | 4/2010 | Tan et al. |
| 2011/0046720 | A1 | 2/2011 | Shalev et al. |
| 2011/0166642 | A1 | 7/2011 | Ehr et al. |
| 2011/0184347 | A1 | 7/2011 | Mason |
| 2011/0319976 | A1* | 12/2011 | Iyer .................. A61F 2/064 623/1.11 |
| 2012/0123451 | A1* | 5/2012 | Asfora ............... A61B 17/08 606/153 |
| 2014/0257369 | A1 | 9/2014 | Leopold et al. |

OTHER PUBLICATIONS

Anneaux et al.; Bioabsorbable polymers as biomaterials; Poster Presentation; 43 pages; This web address was available to applicant(s) at least as of (Aug. 22, 2008).

Eberhart et al.; Bioresorbable polymeric stents: current status and future promise; J. Biomater. Sci. Polymer Edn.; 14(4); pp. 299-312; 2003.

Eggers; Has the incidence of end-stage renal disease in the USA and other countries stabilized?; Curr. Opin. Nephrol. Hypertens.; pp. 20(3); pp. 241-245; May 2011.

Grassmann et al.; ESRD patients in 2004:global overview of patient numbers, treatment modalities and associated trends; Nephrology Dial. Transplant.; 20(12); pp. 2587-2593; Dec. 2005.

Hakaim et al.; Improved patency of prosthetic arteriovenous grafts with an acute anastomotic angle and flow diffuser; J. Vasc. Surg.; 37(5); pp. 1032-1035; May 2003.

Haruguchi et al.; Intimal hyperplasia and hemodynamic factors in arterial bypass and arteriovenous grafts: a review; J. Artif. Organs.; 6(4); pp. 227-235; 2003.

Liou et al.; Intra-aneurysmal flow with helix and mesh stent placement across side-wall aneurysm pore of a straight parent vessel; J. Biomech. Eng.; 126(1); pp. 36-43; Feb. 2004 (Abstract Only).

Malek et al.; Hemodynamic shear stress and its role in atherosclerosis; JAMA; 282(21); pp. 2035-2042; Dec. 1, 1999.

Paryab et al.; Uniform Expansion of a polymeric helical stent; J. Med. Devices; 6(2); May 14, 2012; 1 page; (Abstract only).

Zamir; The role of shear forces in arterial branching; J. Gen. Physiol. Physiology; 67(2); pp. 213-222; 1976.

International Search Report dated Sep. 2, 2013 for Appln. No. PCT/US2013/046370.

\* cited by examiner

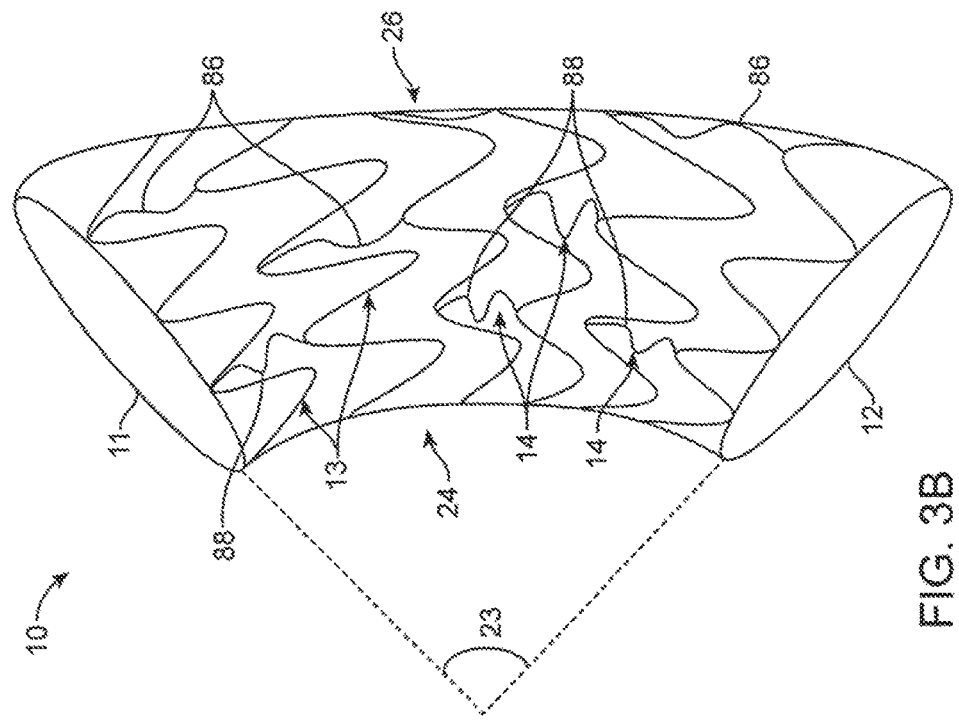
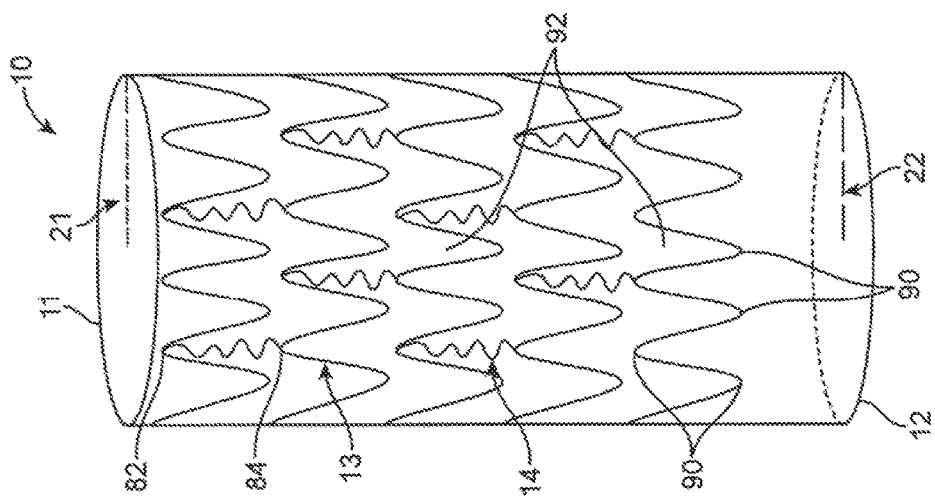
FIG. 3B
FIG. 3A

STENT TO ASSIST IN ARTERIOVENOUS FISTULA FORMATION

CROSS REFERENCE TO RELATED APPLICATIONS

This application is a divisional of U.S. Non-Provisional Application No. 14/409,304, filed Dec. 18, 2014, titled "STENT TO ASSIST IN ARTERIOVENOUS FISTULA FORMATION," which claims the benefit of International Application No. PCT/US2013/046370, filed Jun. 18, 2013, titled "STENT TO ASSIST IN ARTERIOVENOUS FISTULA FORMATION," which claims priority to U.S. Provisional Patent Application No. 61/661,133, filed Jun. 18, 2012, titled "STENT TO ASSIST IN ARTERIOVENOUS FISTULA FORMATION," which is herein incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

FIELD

The present invention relates to stents or other devices used to assist medical personnel in vascular access procedures, particularly those procedures involving the creation of an arteriovenous fistula.

BACKGROUND

Nearly 2.5 million patients worldwide suffer from End Stage Renal Disease (ESRD). To treat ESRD, patients are either subjected to a kidney transplant or undergo hemodialysis. Though acting as artificial kidneys, dialysis machines are not implanted in the body; instead, they require durable external access points to the body's circulatory system, often in the form of an arteriovenous fistula (AVF). An AVF is created via an artificial junction, or "anastomosis", between an artery and a vein which is used to increase the volume of blood flow through the vein. Over time, the increase in blood flow volume increases the size of the vein.

As the circulatory system is typically understood, blood flows away from the heart through a series of arteries. Arteries branch off to even smaller vessels called capillaries, where nutrients such as oxygen are delivered to muscle tissues and cells. Thereafter, deoxygenated blood continues to flow through capillaries, and eventually returns to larger vessels called veins. Veins carry deoxygenated blood back to the heart and lungs, where the blood is reoxygenated and continues through the circulatory system.

In order to create an arteriovenous fistula, this process is short-circuited. There are a number of locations within the body where an arteriovenous fistula may be created, but for hemodialysis patients the most common location is on the non-dominant forearm. In order to create the fistula, the patient is generally put under anesthesia and a small incision is made to open up the patient's forearm in order to expose a superficial vein. The cephalic vein is tied off from blood flow and subsequently severed. The proximal (that is, the segment of the cephalic vein which maintains blood flow to the heart) is then sutured directly to the nearby radial artery and blood flow through the vein is resumed.

Because the normal capillary diffusion system is eliminated, blood flow through the cephalic vein is increased beyond what the vessel is accustomed to. In order to accommodate the increased blood flow, the size of the cephalic vein begins to expand over a period of weeks until the vein itself begins to bulge from under the skin of the patient, a process called AVF maturation. When the bulging vein has reached sufficient size, medical personnel implant dialysis needles into the vein such that dialysis machines can be connected to the patient's circulatory system.

The best hemodialysis vascular access is an Arteriovenous Fistula (AVF). In order to create and AVF, it is required to connect an artery with a vein. After the surgery 6-8 weeks are needed for fistula maturation. During the maturation the venous segment of the fistula is growing. The growing of the vein is triggered by the increased blood flow through the vein. The laminar flow of the blood through the fistula is responsible to initiate a cascade of event leading the fistula vein growth and fistula maturation. Conversely a turbulent blood flow will stimulate the vein to stenose preventing the fistula from maturing.

Unfortunately, there are a number of complications that may occur in the creation of an arteriovenous fistula. For example, the typical AVF requires 6-8 weeks to mature to a size and strength sufficient to support insertion of a dialysis needle. Further, 45-55% of AVFs fail to sufficiently mature, requiring the creation of a new arteriovenous anastomosis and a further 6-8 weeks of maturation time before a new fistula is created.

Many of the AVF created do not mature to a usable AVF. In US, the AVF maturation rate ranges between 45-55%. Most of the times the cause of nonmaturation is the presence of perianastomotic stenosis (narrowing of the vessel in the area of the surgical anastomosis) found to be present in 75% of nonmaturing AVF. The trauma of the surgery and the turbulent blood flow are believed to be responsible for the development of perianastomotic stenosis. The turbulent flow involved in the lack of fistula maturation might be created by the steep angle the vein is anastomosed to the artery. FIG. 1 illustrates the current situation. There is shown an arteriovenous anastomosis D formed by an artery B and a vein C. There is a panastomosis B formed in the vein C vein. Note as well the steep angle of the anastomosis D.

AVF developmental complications are generally attributed to increases in blood flow shear stress, i.e. turbulence, created due to the artificial nature of the arteriovenous anastomosis. As the blood flows through the artery and into the vein, it has been observed to eddy, or pool, instead of flowing smoothly through the anastomosis. This turbulent flow causes blood vessel stenosis—a narrowing of the vessel which limits the available flow rate. As stenosis occurs in the fistula anastomosis, the volume of blood flow is reduced, and the vessel may fail to stretch to the volume required to support a dialysis access port. It is therefore desirable to design a device which minimizes the amount of turbulent blood flow through the AVF anastomosis.

SUMMARY OF THE DISCLOSURE

In one embodiment of the present invention, a stent used for placement within an arteriovenous anastomosis is provided. The stent may be composed of a polymeric material selected from a number of biodegradable compounds which are identified based on their in vivo degradation rate, biocompatibility, malleability, or other relevant characteristics. The stent may further include a series of sinusoidal-shaped struts which circle the stent transversely. These struts may be operably connected to each other by collapsible supports which run longitudinally down the length of the stent.

In another embodiment of the present invention, the stent is shaped to form a conical trunk, wherein the distal aperture of the stent has a greater circumference than the proximal aperture.

In yet another embodiment of the present invention, the distal end of the stent includes hooks or barbs used to securely fasten the stent to the artery at the site of anastomosis.

In yet another embodiment of the present invention, the stent may be bent or curved such that is adopts an angle of anastomosis which promotes laminar, non-turbulent, blood flow through the arteriovenous interface.

In general, in one embodiment of the present invention, an arteriovenous fistula stent includes a tubular body comprising a series of sinusoidal shaped struts along the length of the tubular body. The arteriovenous fistula further includes a plurality of curvilinear connectors extending between and attached to adjacent struts wherein a first end of a connector is attached to a distal face of a proximal strut apex and a second end of a connector is attached to a proximal face of a distal strut apex with a pair of unconnected strut apexes between pairs of connected apexes, wherein when the tubular body is in a stowed configuration a proximal aperture and a distal aperture are circular and when the tubular body is in a deployed configuration the distal aperture is oblong or ovoid.

This and other embodiments can include one or more of the following features. For example, the tubular body can be constructed of a biocompatible polymer selected from the group consisting of a (poly)lactic acid, a poly(lactic-co-glycolic acid), a polyglycolide, a copolymer, and a cross-linked polymer. In another aspect, the tubular body can be constructed from a biocompatible polymer having an in vivo degradation rate corresponding to the time required for fistula formation. In still another aspect, the curvilinear connectors can have a zig-zag shape. In a further aspect, the curvilinear connectors can have a wave shape. In yet another aspect, when the stent is in a deployed configuration a distal aperture of the stent can have a non-circular opening. In another aspect, the distal aperture can have a circumference and a shape selected based on an anastomosis angle of the stent in use to form an arteriovenous fistula. In still another aspect, when the stent is in a deployed configuration shaped into a curvature angle for use to form a fistula, a portion of the curvilinear connectors along an inner radius of the curvature angle can be shorter than a portion of the curvilinear connectors along an outer radius of the curvature angle. In a further aspect, when the stent is formed to facilitate formation of an arteriovenous fistula the stent has a tilted conical trunk and an obtuse curvature angle. In yet another aspect, when the stent is formed to facilitate formation of an arteriovenous fistula a distal aperture of the stent can have an ovoid or oblong shape. In a further aspect, in use to facilitate formation of an arteriovenous fistula, there can be a circular opening on the proximal end of the tubular body and a non-circular opening on the distal end of the tubular body. In yet a further aspect, in use to facilitate formation of an arteriovenous fistula, the circumference of a proximal end of the tubular body can be less than the circumference of a distal end of the tubular body. In another aspect, the stent includes an interwoven mesh of biocompatible polymer materials about the tubular body.

In general, in one embodiment, a method for inserting a stent for use in creation of an arteriovenous fistula, includes the steps of identifying a candidate artery and a candidate vein, dissecting the candidate vein, inserting a stent into the vein, creating a breach in the candidate artery at a desired angle and location, introducing the stent and vein into the candidate artery, forming the stent into a curvature angle selected to minimize turbulent blood flow in an anastomosis formed by the vein and the artery and fastening a distal portion of the stent to the artery to form an anastomosis.

This and other embodiments can include one or more of the following features. In one aspect, after the fastening step the anastomos can be formed by the vein and the artery forms an anastomosis angle between 90 degrees and 180 degrees. In another aspect, the anastomosis angle can be between 100 degrees and 130 degrees. In yet another aspect, the fastening step can further include engaging a fastener on the distal portion of the stent with a portion of the artery. In still another aspect, the fastening step can further include suturing the distal portion of the stent to the artery. In another aspect, the method can further include using an angioplasty balloon to expand the vein before or after the inserting step. In yet another aspect, after the forming step a portion of the stent can be compressed and portion of the stent is expanded. In a further aspect, after the forming step or the fastening step a circumference of the distal aperture of the stent attached to the artery can be larger than a circumference of the proximal aperture of the stent within the vein. In another aspect, after the forming step or the fastening step the distal aperture of the stent attached to the artery can be configured into an imperfectly circular shape. Still further, the vein can be a cephalic vein and the artery can be a radial artery. In another aspect, the forming step can further include applying heat to the stent. In yet another aspect, the method can further include applying pressure to the stent. In still another aspect, the forming step can be performed by inserting and inflating a balloon inserted into the stent. In another aspect, the method can further include forming the desired anastomosis angle by inserting a shape tool into the distal aperture.

In one embodiment there is provided a device for use in the creation of an arteriovenous fistula. The device includes a generally cylindrical stent, which may be deformed to assume a desired curvature, wherein said tube is configured for attachment to a vein at its proximal aperture and to an artery at its distal aperture. In another aspect, the exterior of the tube is bound to a series of support struts which travel transversely along the exterior of the tube and extend from the proximal aperture to the distal aperture. In another alternative, each strut in the series is linked by extendable connector. In still other aspects, the distal aperture is configured to contain a fastening element which may be used to securely fasten the distal aperture to the desired artery. In some embodiments, the fastening element is a hook. In still other alternatives, the distal aperture is connected to the desired artery at an angle selected to minimize turbulent blood flow in the arteriovenous anastomosis, the angle is between 90 and 180 degrees. In another aspect, the tube may assume a generally conical shape, where the circumference of the proximal aperture is less than the circumference of the distal aperture and, in one embodiment, the desired curvature is achieved by subjecting the tube to an external stimulus.

In still another aspect, there is provided a method for inserting a stent for use in creation of an arteriovenous fistula. The method includes identifying a candidate artery and a candidate vein; dissecting the candidate vein, using an angioplasty balloon to expand the vein; inserting a stent into the vein; creating a breach in the candidate artery at a desired angle and location; introducing the stent and vein into the candidate artery; and fastening the stent to the artery. In one alternative, the stent's configuration is modified by the application of an external stimulus prior to insertion into the candidate artery.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 3A displays the stent (without fixation elements) in its natural, undeformed state. FIG. 3B displays the stent of FIG. 3A in a bent or deformed state.

DETAILED DESCRIPTION

Figure 1:
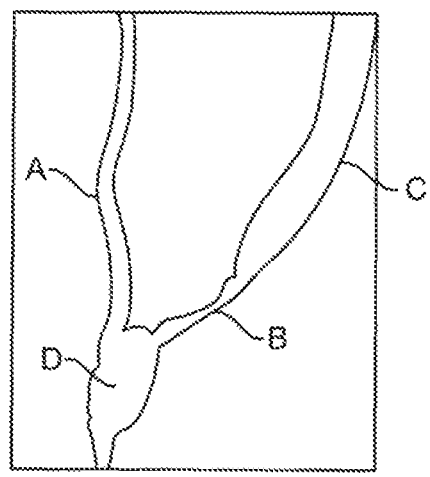
FIG. 1 is a top view of a failed arteriovenous anastomosis formed between a vein and an artery.

A stent used in creation of an arteriovenous fistula is now described. While the stent may be used in the creation of a fistula at any location in the body desired by the physician, the ensuing description shall generally refer to a creation of a radiocephalic fistula. A radiocephalic fistula is a fistula created by an anastomosis between the cephalic vein and radial artery of the forearm. As such, any specific reference to a radiocephalic fistula should not be read to limit the scope of the invention.

Anatomical studies show that all the arteries in the body are branching from the main artery through an obtuse angle to allow a laminar, physiologic blood flow. Also the shape of the arterial bifurcations—a tilted conic trunk—allows for a smooth connection and a laminar blood flow that is beneficial to the arterial function. The shape and "gentle angles" of bifurcations of the arteries in the body are a testimony that this is the most efficient way to ensure a good function of the vascular tree. Described herein are various stent designs to create an anastomosis of the vein with the feeding artery that mimic the natural arterial bifurcation. Exemplary components of the stent include a curved or straight cylindrical structure at the venous part and a tilted conic trunk. The tilted conic trunk is selected to mimic the shape of arterial bifurcations and to create an angle of bifurcation with the artery that is not acute. Optionally, hooks may be provided at the arterial side to connect the vein to the artery without the need for a suture.

In one aspect, embodiments of the invention are designed to help in creating an arteriovenous anastomosis that mimics the shape of the natural arterial bifurcations, ensure a physiologic angle of the arteriovenous anastomosis, decreases the operative time and maximizes the maturation rate of the AVF. In one aspect, the stent is designed to be made of a bioresorbable material, so after the AVF maturation it will disappear and will minimize the impact on the arteriovenous fistula. While desiring not to be bound by theory, it is expected that the embodiments of the stent described herein will increase the fistula maturation rate by improving the shape of the arteriovenous anastomosis and will make a more physiologic connection between the artery and the vein and thus minimizing the complications.

The stent may be composed of a polymeric material, or combinations of polymeric materials. The polymers used to form the stent may possess attributes that make them particularly suitable for use within the body. For example, in some embodiments, the polymers used to create the stent may be biocompatible. In some cases, the polymers may also be biodegradable. Further, the polymers may be selected for their ability to irreversibly deform or bend in order to assume a desired shape. Moreover, the polymers may be sufficiently elastic to allow for body movement, but rigid enough to support body tissues under pressure. In some embodiments of the invention, the polymers are comprised of composite materials, including copolymers, cross-linked polymers, or similar constituents which may be selected based on any of the foregoing criteria. Polymeric materials may also be selected for their temperature-dependent properties including, but not limited to, malleability and tensile strength.

In one embodiment, biodegradable polymers are preferred in that a biodegradable stent as described herein provides the curvature angle to the nascent anastomosis without retarding maturation of the fistula. A conventional stent design that persists (i.e., non-degradable) continues to hold open the lumen of a blood vessel but also limits the maturation of the fistula by constraining the size of the blood vessel. In contrast, as the biodegradable stent degrades, the stent will not impair the maturation of the fistula and permits maturation across the entire fistula.

Figure 2A:
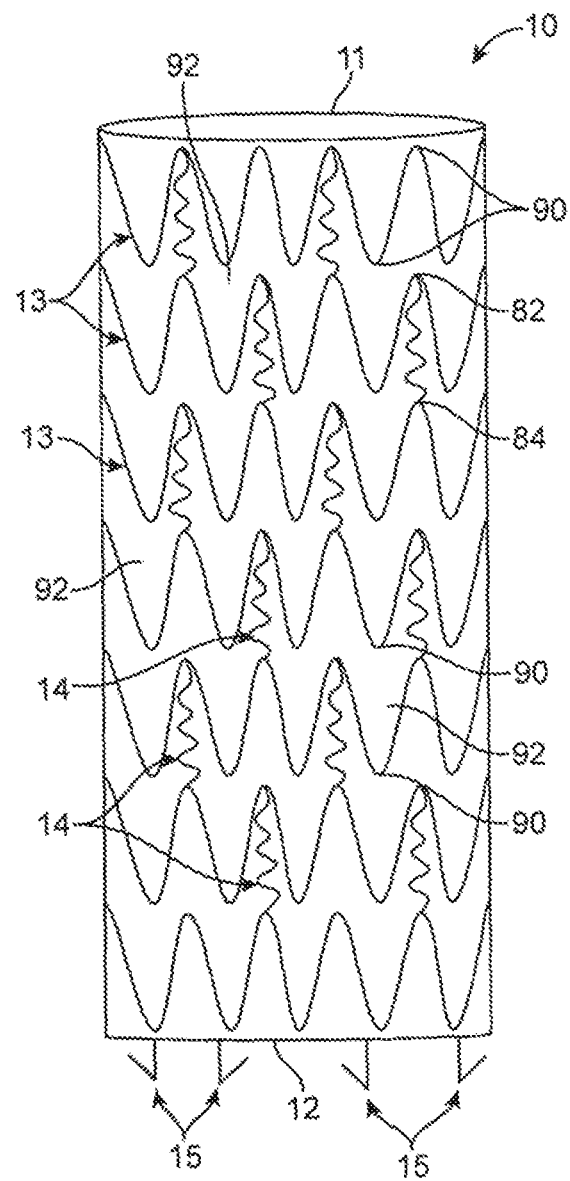
FIG. 2A displays the structure of the stent (with fixation elements) in a natural undeformed state and FIG. 2B illustrates the stent of FIG. 2A in a bent or deformed state.

Examples of stents and methods associated with their implantation in the body are now provided. In particular, compositions and methods for forming an arteriovenous fistula within the body are described in connection with a set of embodiments. FIG. 2A displays a schematic illustration of the stent as it exists in its natural (i.e. outside of the body) state. As used herein, the term "proximal" shall refer to the end of the stent which interfaces with a vein, white the term "distal" shall refer to the end of the stent which interfaces with an artery. Further, the term "artery" shall mean any blood vessel in the body which carries blood away from the heart, while the term "vein" shall mean any blood vessel which carries blood to the heart.

FIG. 2A displays stent 10, which is generally cylindrical in shape and includes a proximal aperture 11 and a distal aperture 12. In one embodiment of the invention, stent 10 is a solid tube constructed of a biocompatible polymer including, but not limited to, (poly)lactic acid, poly(lactic-co-glycolic acid), polyglycolide, or copolymers, cross-linked polymers, or composite compounds thereof. In some embodiments, the biocompatible polymer is selected for its in vivo degradation rate which may align with the time required for adequate fistula formation. In other embodiments, the biocompatible polymer is selected for its tensile properties or heat-dependent malleability profile. In additional embodiments of the invention, stent 10 is comprised of an interwoven mesh of biocompatible polymer materials and support struts 13. Stent 10 need not be perfectly fluid impermeable, but it in any embodiment it must retain sufficient structural rigidity to shape an anastomosis. Proximal aperture 11 may be configured for attachment to any blood vessel carrying blood to the heart, such as the cephalic vein. Distal aperture 12 is configured such that it can be attached to any blood vessel carrying blood away from the heart, such as the radial artery. In some embodiments, distal aperture 12 is configured in an imperfectly circular shape, such that it may securely interface with a desired artery when stent 10 is not perpendicularly affixed to the artery.

Figure 8:
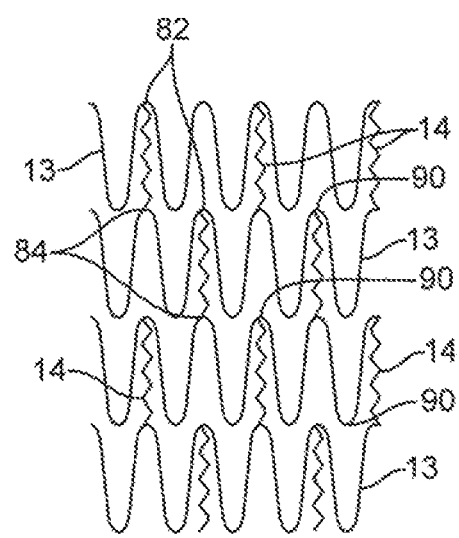
FIG. 8 illustrates a section view of the struts, connectors and apexes the stents shown in FIGS. 2A and 3A.

Continuing in FIG. 2A, the exterior surface of stent 10 is circumnavigated by a series of sinusoidal-shaped struts 13, which cover the exterior of stent 10 lengthwise from the proximal aperture 11 to distal aperture 12. As illustrated in the various embodiments, the struts include a plurality of apexes 90. Struts 13 may be composed of any biocompatible material that is sufficiently malleable to permit deformation of stent 10, yet is rigid enough to hold stent 10 in a desired deformed configuration. Individual struts 13 are linked by connectors 14. In some embodiments, connectors 14 link the struts 13 by attaching a portion of one apex 90 on one strut 13 to another apex 90 on an adjacent strut. In one configuration, the distal face of a proximal strut apex 82 is connected to the proximal face of a distal strut apex 84. An unconnected apex 92 is an apex 90 without a connector 14. FIG. 8 illustrates a section view of the struts 13, connectors 14, apexes 90, distal and proximal faces of apexes 82, 84 as well as unconnected apexes 92 shown in the stent embodiments of FIGS. 2A and 3A (stent 10 in an undeformed or stowed configuration).

In some configurations, unconnected apexes 92 are positioned adjacent one another forming an alternating pattern of connected and unconnected apexes as shown in the various embodiments. In further embodiments, connectors 14 are attached to an apex 90 of adjoining struts at alternating transverse apices. In some embodiments, connectors 14 may have a wave-like or "zig-zag" shape in linking adjacent struts 13. In further embodiments of the invention, connectors 14 have a configuration designed to support struts 13 when stent 10 is in a non-deformed state while maintaining sufficient flexibility to operably support struts 13 when stent 10 assumes a deformed state. As a result, some connectors 14 will be expanded connectors 86 and some will be compressed connectors 88 (see, e.g., FIG. 3B). In additional embodiments of the invention, connectors 14 may assist struts 13 in maintaining a desired deformation of stent 10.

Figure 2B:
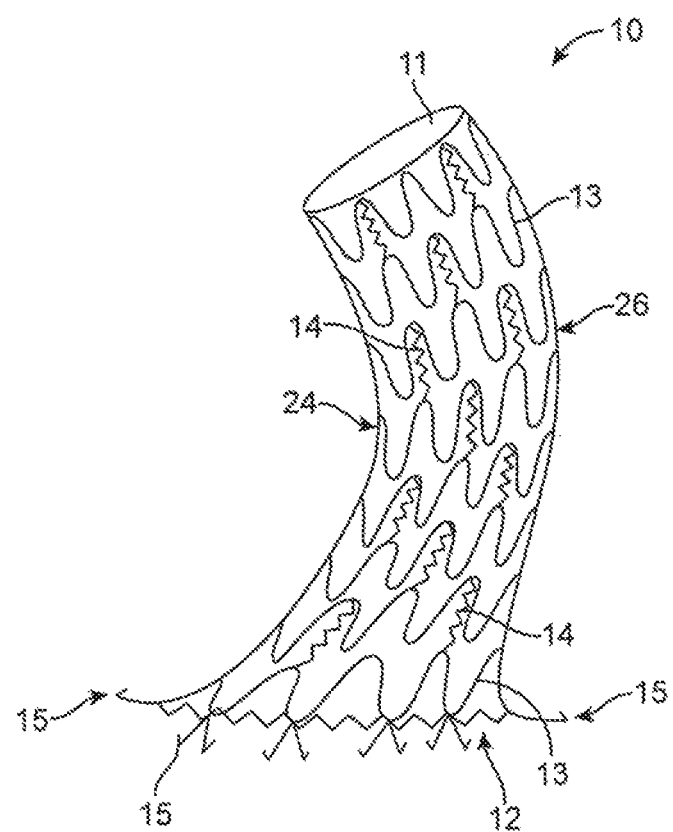

Also in FIG, 2A, the distal aperture 12 may also be configured to contain a fastener 15. The fastener 15 may be composed of any means useful for irreversibly attaching the stent 10, at the distal aperture 12, to a desired artery. The fastener 15 may be comprised of hooks, barbs, clamps, or similar mechanisms which may be utilized to secure the interface between the distal aperture 12 and the desired artery. FIG. 2B illustrates the stent of FIG. 2A in a bent or deformed state also referred to as the deployed or implanted state of the stent. FIG. 2B illustrates the zigzag connectors 14, the curved cylinder towards the proximal aperture 11 along with inner radius 24 and outer radius 26. There is also illustrated the tilted cone trunk near the distal aperture 12.

Turning now to FIG. 3A, an embodiment of stent 10 in its natural, non-deformed state is depicted. In one embodiment, the cylindrical stent 10 may assume a generally conic nature, wherein proximal aperture 11 has a proximal radius 21 and the distal aperture 12 has a distal radius 22. In some embodiments of the invention, proximal radius 21 is less than distal radius 22. It will be recognized by those skilled in the art that the ratio of proximal radius 21 to distal radius 22 can assume a range of potential values while stent 10 remains viable for implantation into the body. All such potentially viable ratios are hereby incorporated into the invention. In a preferred embodiment of the invention, the ratio of proximal radius 21 to distal radius 22 is selected such that laminar blood flow through stent 10 is facilitated. In other embodiments of the invention, proximal aperture 11 and distal aperture 12 may assume an ovoid, oblong, or otherwise imperfectly-circular shape. In such embodiments, the circumference of proximal aperture 11 may be less than the circumference of distal aperture 12 (see e.g., FIGS. 4, 6 and 7). In some embodiments of the invention, the characteristics of proximal aperture 11, proximal radius 21, distal aperture 12, and distal radius 22 may be modified by subjecting all or part of stent 10 to an external stimulus (e.g. a heat source), and/or physically manipulating the shape or size of proximal aperture 11 or distal aperture 12 based on the heat-dependent malleability characteristics of the selected polymeric material.

Stent 10 may also bend to assume a deformed or curved shape upon implantation in the body, as shown in FIG. 3B. In one embodiment, stent 10 may be deformed such that the plane extending radially from proximal aperture 11 intersects with the plane extending from distal aperture 12 at a curvature angle 23. Curvature angle 23 may assume any range of values front 0 to 180 degrees. In a preferred embodiment, curvature angle 23 assumes the deformation necessary to facilitate the desired anastomosis angle 36 depicted in FIG. 4. In other embodiments of the invention, the curvature angle 23 may be defined by the intersection of additional references planes which extend from the surface of the stent 10 at locations intermediate between proximal aperture 11 and distal aperture 12. In some embodiments of the invention, stent 10 may be exposed to an external stimulus (e.g. a heat source) and be physically manipulated into the desired curvature or deformation.

Figure 4:
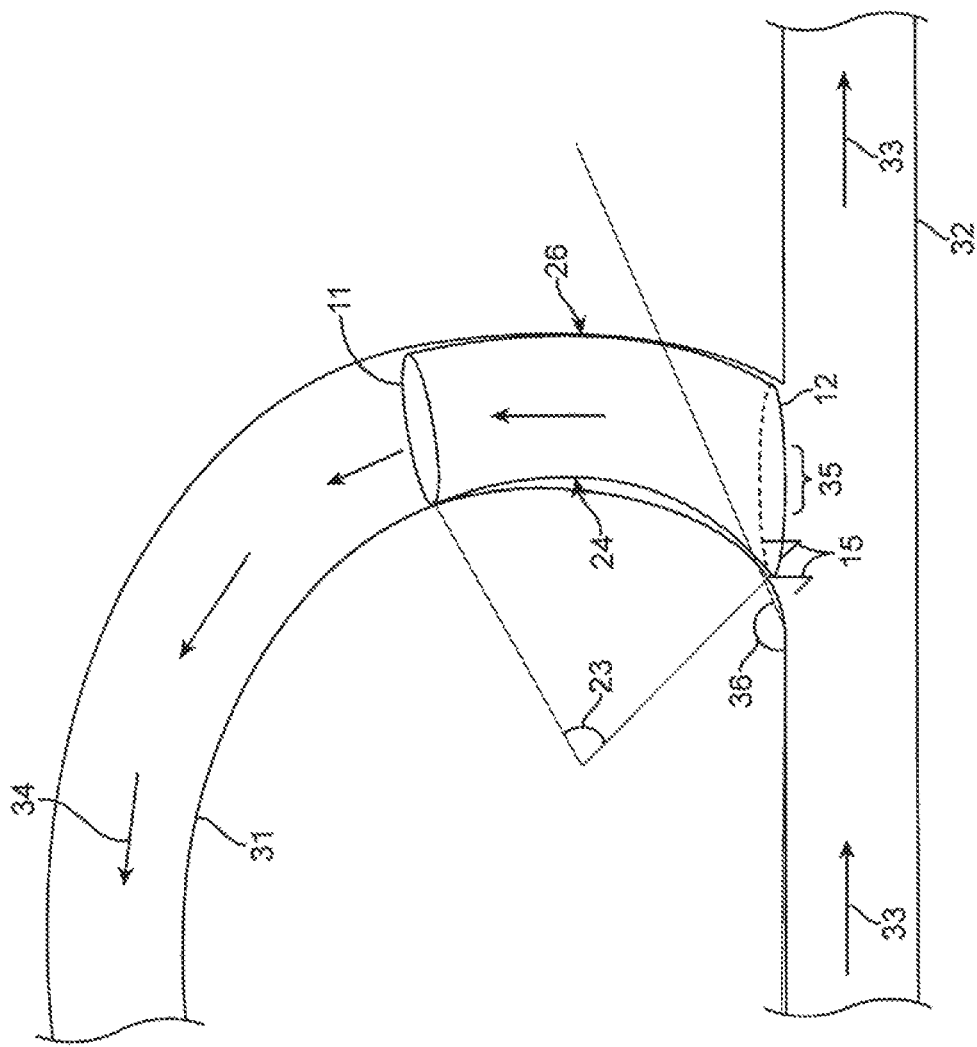
FIG. 4 displays a stent similar to the stent of FIG. 2B as it appears when implanted into the body to form an arteriovenous anastomosis.

FIG. 4 displays stent 10 as it appears when implanted into the body to assist in formation of an arteriovenous anastomosis 35. In one embodiment, the stent 10 is implanted in vein 31 and deformed to assume curvature angle 23. Stent 10 is then configured to attach to artery 32 at the distal aperture 12 in order to form arteriovenous anastomosis 35. In some embodiments, stent 10 may be securely fastened to artery 32 by fastening element 15 at arteriovenous anastomosis 35.

Stent 10 may be attached to artery 32 at an anastomosis angle 36. In a preferred embodiment, anastomosis angle 36 is selected such that turbulence in blood flow through stent 10 is minimized as the blood flow divides into venous blood flow 34 and arterial blood flow 33. Anastomosis angle 36 is defined as the angle of insertion of the stent 10, at proximal aperture 12, as it interfaces artery 32 at the arteriovenous anastomosis 35. The anastomosis angle 36 may be between about 90 degrees and 180 degrees and is preferably between about 100 degrees and 130 degrees.

Figure 9:
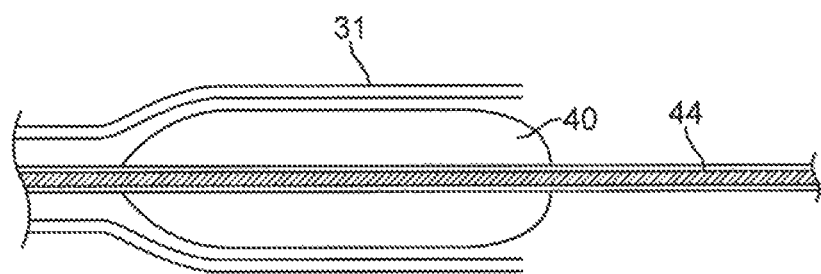
FIG. 9 is a section view of a guide wire and balloon inserted into a vein.

In order to implant the stent, a candidate vein (e.g. the cephalic vein) and a candidate artery (e.g. the radial artery) must be identified. The candidate vein may be dissected and the distal segment of the candidate vein may be ligated. A wire may then be inserted into the proximal segment of the candidate vein. Over the wire, a first angioplasty balloon may be inserted and a low pressure angioplasty of the distal-most end of the proximal segment of the candidate vein is performed. FIG. 9 is a section view of a guide wire 44 and balloon 40 inserted into a vein. The first angioplasty balloon may then be removed. The angioplasty balloon 40 may be of any diameter known in the art and may be selected based on the size of the vein and/or the stent to be used in the procedure.

Figure 10:
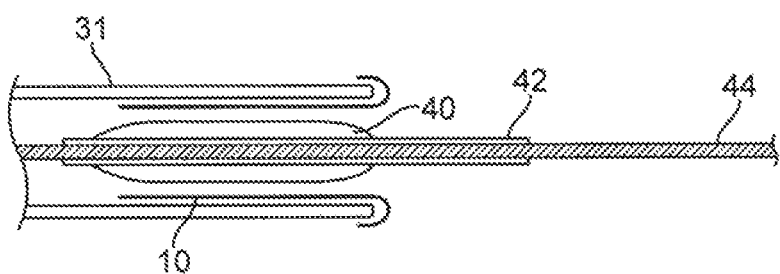
FIG. 10 is a section view of a stent introduced into the distal end of the vein shown in FIG. 9.
Figure 11:
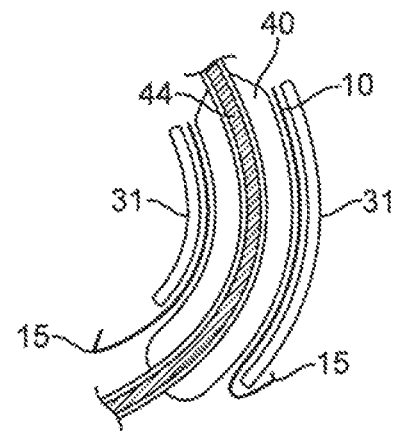
FIG. 11 is a section view of a balloon within the stent inflated to create a curvature in the stent.

The collapsed stent 10 may then be loaded over a second angioplasty balloon, which is subsequently inserted into the proximal segment of the dissected candidate vein. The angioplasty balloon 40 may be advanced such that stent 10 is placed completely inside the candidate vein, with only fasteners 15 extending outside of the proximal candidate vein segment. FIG. 10 is a section view of a stent 10 introduced into the distal end of the vein 31 shown in FIG. 9. The stent 10 is carried on the balloon 40 and balloon catheter 42 along wire 44. The second angioplasty balloon may then be inflated to expand the stent 10 inside the proximal segment of the candidate vein. FIG. 11 is a section view of a balloon 40 within the stent 10 inflated to create a curvature 23 in the stent.

Figure 12:
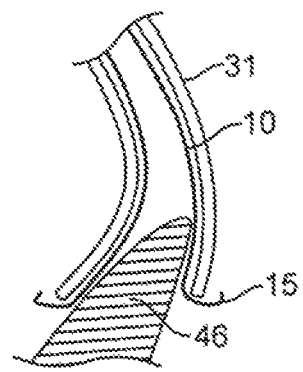
FIG. 12 is a section view of a conic shaped tool inserted into the distal end of the stent to create the shape of the anastomotic part of the stent.

When the second angioplasty balloon is inflated at low pressure, the stent 10 may be physically manipulated to assume the desired curvature angle 23. In some instances, an external stimulus, such as heat, may be applied to facilitate the physical deformation of stent 10 to curvature angle 23. Curvature angle 23 may be identified based on the requisite anastomosis angle 36 necessary to minimize turbulent blood flow through the anastomosis 35. At this time, an external stimulus such as heat or physical force may be applied to the distal aperture 12 of stent 10 to configure distal aperture 12 and/or distal radius 22 to the parameters necessary to minimize turbulent blood flow through the anastomosis 35. In another aspect, the distal opening of the stent may be shaped to form the desired anastomosis angle. FIG. 12 is a section view of a conic shaped tool 46 inserted into the distal end 12 of the stent 10 to create the shape of the anastomotic part of the stent (e.g., angle 36 and shape of opening 12).

Figure 13:
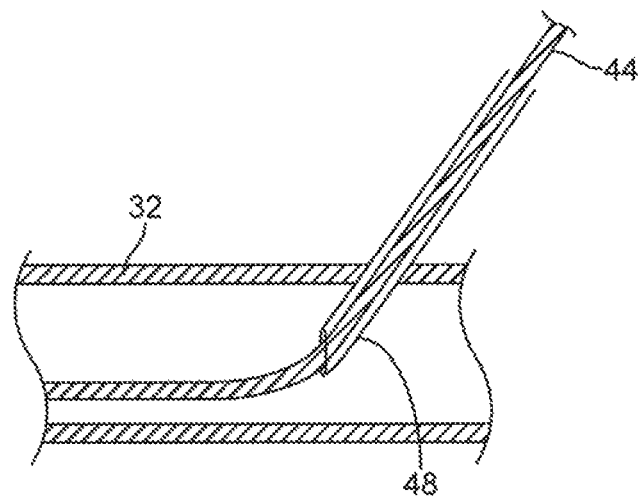
FIG. 13 is a section view of a needle and guide wire accessing a candidate artery.
Figure 14:
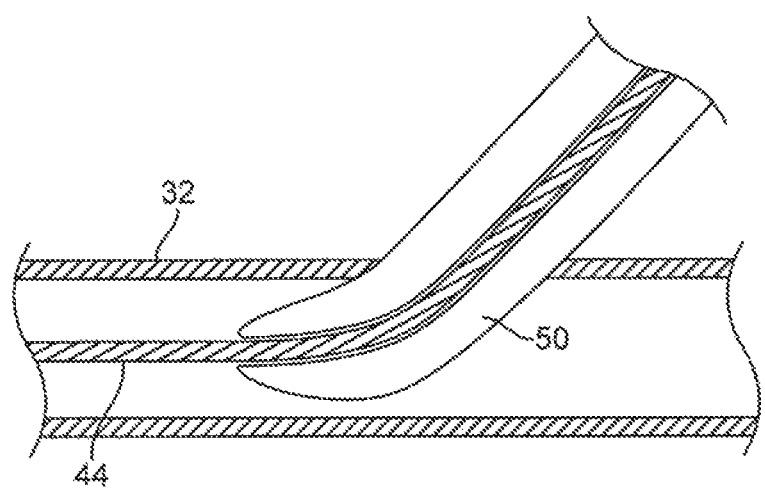
FIG. 14 is a section view of a dialator enlarging the opening in the candidate artery.

The identified candidate artery may then be accessed with a needle in the area of the desired location of the anastomosis. FIG. 13 is a section view of a needle 48 and guide wire 44 accessing a candidate artery. Via the needle 44, a wire may be introduced to the artery at the desired anastomosis angle 36. A dilator 50 may then be extended over the wire 44 and serial dilation of the artery with an appropriate-sized dilator may then be performed in order to create an arterial breach. FIG. 14 is a section view of a dilator 50 enlarging the opening in the candidate artery.

Figure 15:
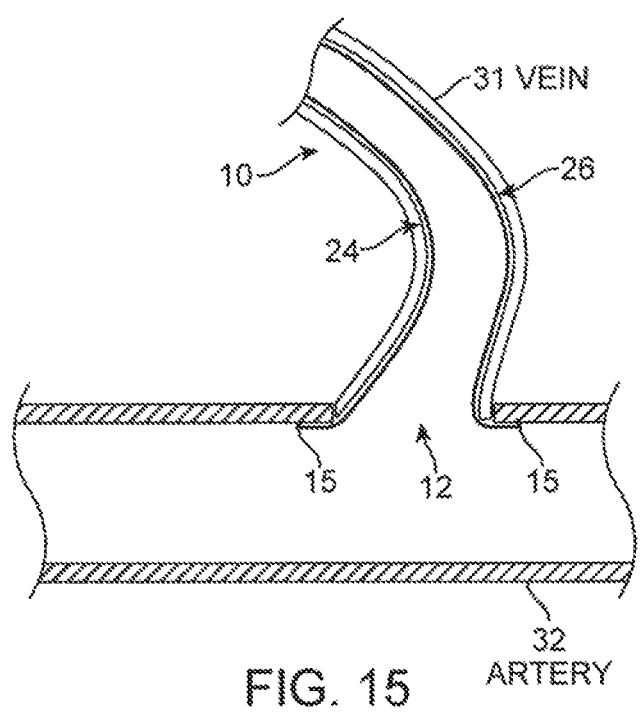
FIG. 15 is a section view of a distal part of a stent introduced into a candidate artery.

Through the arterial breach, while ensuring hemostasis, the distal aperture 12 of stent 10, along with the attached proximal segment of the candidate vein 31, may be introduced into the artery. After insertion, stent 10 may be retracted such that fasteners 15 connect with the arterial wall 32. If needed, sutures may then be applied to the exterior of anastomosis 35 to ensure hemostasis. FIG. 15 is a section view of a distal part of a stent 10 introduced into a candidate artery 32.

Figure 5:
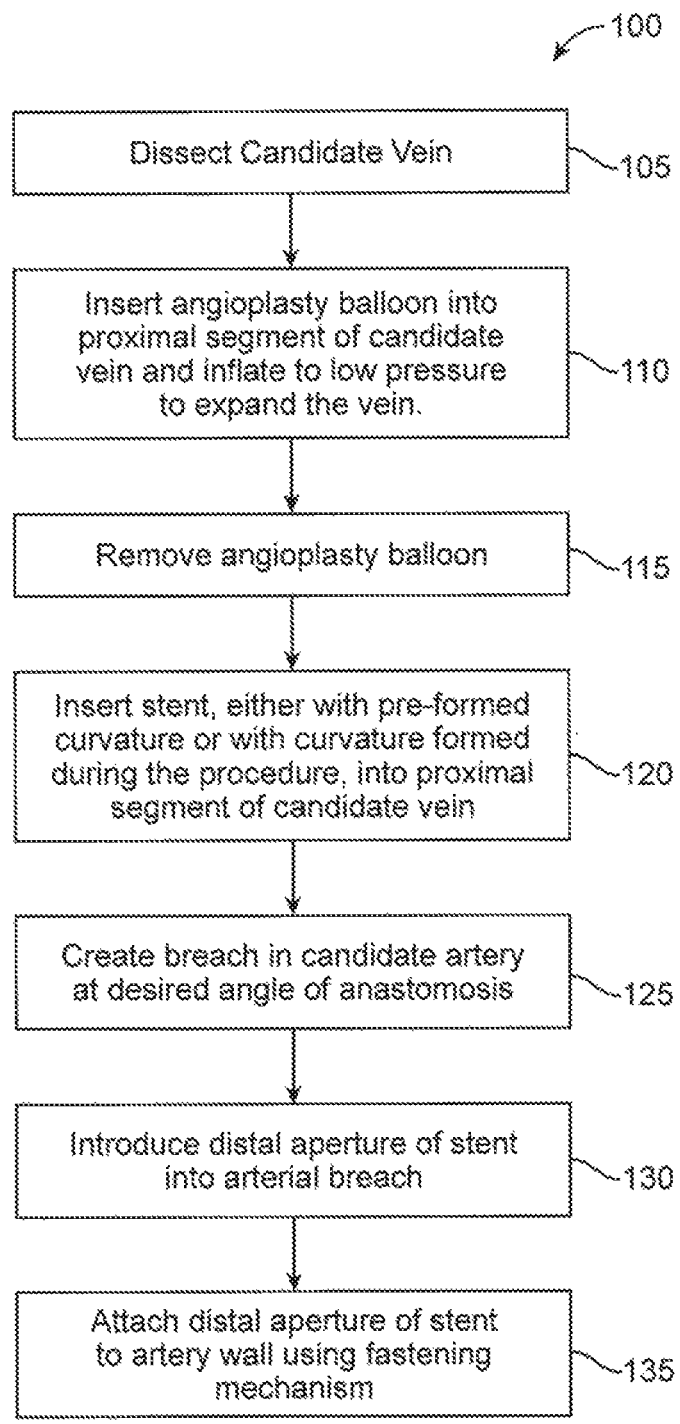
FIG. 5 exhibits the method utilized to implant the stent within the body in order to facilitate creation of an arteriovenous fistula.

FIG. 5 depicts a method 100 which may be utilized to implant the stent within the body. At step 105, dissect candidate vein. Insert angioplasty balloon into proximal segment of candidate vein and inflate to low pressure to expand the vein (step 110). Thereafter, remove the angioplasty balloon (step 115). Then, insert the stent, either with pre-formed curvature or with a curvature formed during the procedure, into a proximal segment of candidate vein. At step 125, create a breach in candidate artery at a desired angle of anastomosis. Then, introduce a distal aperture of stent into the arterial breach (step 130). Thereafter, attach distal aperture of stent to artery wall using fastening mechanism (step 135). In one aspect, the fastening mechanism is one or more hooks or fixation elements about the distal aperture as when used with embodiments of FIGS. 2A and 2B. In another aspect, the fastening mechanism comprises a suture to appropriately join the distal aperture to the artery as when used with embodiments of FIGS. 3A and 3B.

Figure 6:
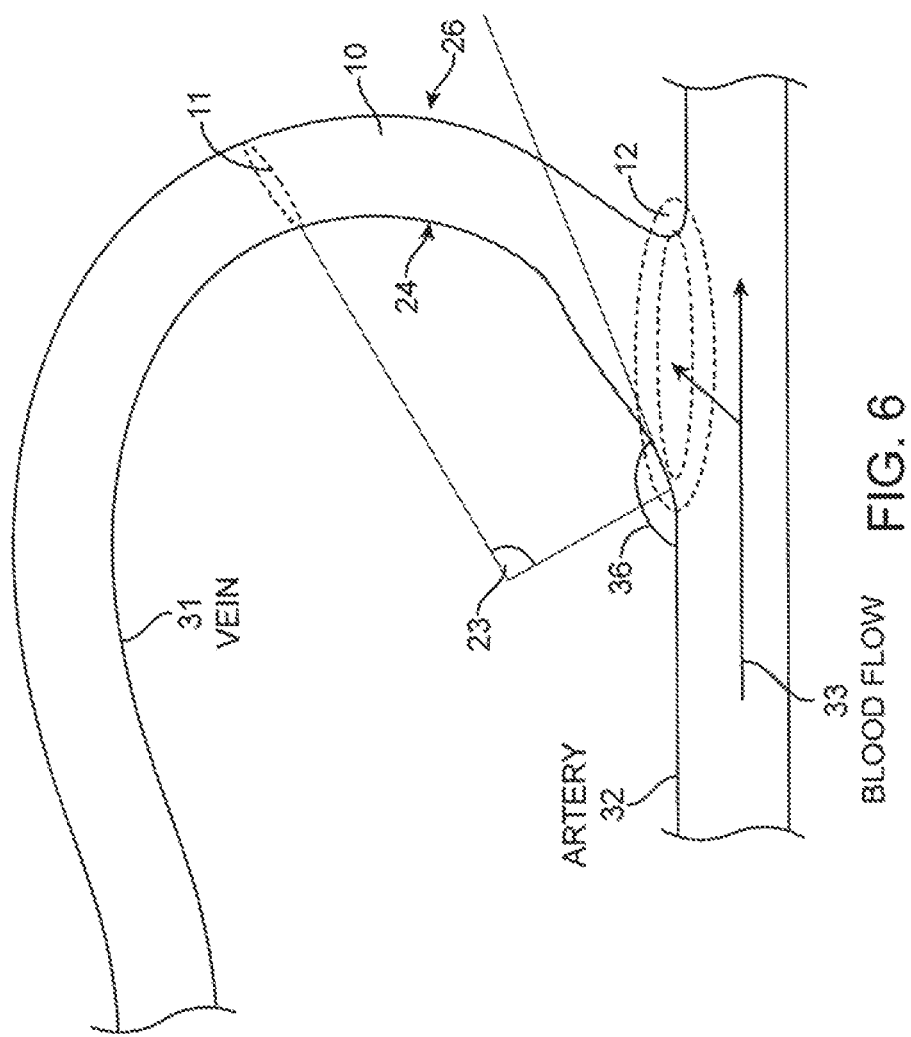
FIG. 6 displays a stent similar to the stent of FIG. 3B as it appears when implanted into the body to form an arteriovenous anastomosis.

FIG. 6 displays a stent similar to the stent of FIG. 3B as it appears when implanted into the body to form an arteriovenous anastomosis. As illustrated in this embodiment, the distal aperture 12 has a larger circumference (shown in phantom) than the proximal circumference 11 (shown in dashed ones). The stent position illustrated also provides another illustrative configuration of the anastomosis angle 36 and angle of curvature 23 with inner radius 24 and outer radius 26. This view also illustrates the tilted conic trunk.

Figure 7:
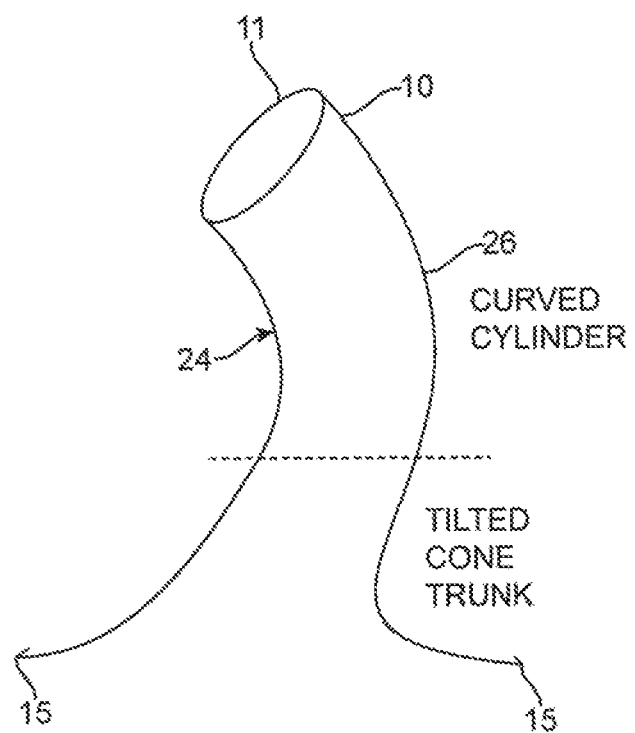
FIG. 7 illustrates an embodiment of a stent having a distal end with a tilted cone trunk and a proximal portion formed into a curved cylinder.

FIG. 7 illustrates an embodiment of a stent having a distal end with a tilted cone trunk and a proximal portion formed into a curved cylinder.

There is described various embodiments of a specially designed stent to create an anastomosis of the vein with the feeding artery that mimic the natural arterial bifurcation. In one aspect, the components of the stent include a curved or straight cylindrical structure at the venous part; a tilted conic trunk to mimic the shape of arterial bifurcations and to create an angle of bifurcation with the artery that is not acute; and hooks at the arterial side to connect the vein to the artery without the need for the suture.

In still other embodiments, other stent features are provided, such as, the connectors of the stent struts are not straight but zigzagged to allow for the stent to assume a curved shape to optimize the blood flow. Zigzagged connectors to allow for the stent to assume a curved shape (below) where some connectors are compressed and some are expanded (see, for example, FIG. 3B).

In still other embodiments, hooks are provided. The arterial part of the stent ends with a row of hooks that are meant to allow the connection of the stent with the artery, obviating the need for suture. The hooks emerge from the body of the stent at an angle that will allow them to enter the arterial wall and connect the stent to the artery.

The stent structure may take several different forms in the various embodiments. For example, the stent may include a curved cylinder toward the venous side—to ensure a smooth curvature of the fistula. In still another aspect, there is a tilted conic trunk toward the arterial side to ensure an obtuse angle of the fistula with the feeding artery and to ensure a connection that mimic the natural shape of the arterial bifurcations. Still further, there is provided zigzagged connectors to ensure the stent can assume a curved position with hooks that anchor the arterial part of the stent to the arterial wall. There is also provided proposed operative steps to create a AVF using an embodiment of a stent described herein. In still other aspects, there is a combined curved and conic shape of the stent providing a stent whose shape can be customized as needed for the successful formation of a desired arteriovenous fistula. In one aspect, the stent includes zigzagged connectors to ensure a curved shape and hooks to ensure the arterial anastomosis. Stilt further, the curved and conic shape of the stent is meant to ensure a physiologic bifurcation in terms of shape and angle.

What is claimed is:

1. A method for inserting a stent for use in creation of an arteriovenous fistula, comprising the steps of:
   identifying a candidate artery and a candidate vein;
   dissecting the candidate vein;
   inserting a stent into the candidate vein to form a stent and vein structure, the stent having a tubular body constructed from a biocompatible polymer with an in vivo degradation rate corresponding to the time required for fistula maturation;
   creating a breach in the candidate artery at a desired angle and location;
   after forming the stent and vein structure, introducing the stent and vein structure into the candidate artery;
   applying heat from an external heat source and pressure to the stent and vein structure to shape the stent and vein structure into a curvature angle selected to minimize turbulent blood flow in an anastomosis formed by the candidate vein and the candidate artery; and
   fastening a distal portion of the stent and vein structure to the candidate artery to form an anastomosis.

2. The method of claim 1 wherein after the fastening step the anastomosis formed by the candidate vein and the candidate artery forms an anastomosis angle between 90 degrees and 180 degrees.

3. The method of claim 2 wherein the anastomosis angle is between 100 degrees and 130 degrees.

4. The method of claim 1 the fastening step further comprising: engaging a fastener on the distal portion of the stent with a portion of the candidate artery.

5. The method of claim 1 the fastening step further comprising: suturing the distal portion of the stent to the candidate artery.

6. The method of claim 1 further comprising: using an angioplasty balloon to expand the candidate vein before or after the inserting step.

7. The method of claim 1 wherein after applying heat from an external heat source and pressure to the stent and vein structure, a portion of the stent is compressed and portion of the stent is expanded.

8. The method of claim 1 wherein after the fastening step a circumference of the distal aperture of the stent attached to the candidate artery is larger than a circumference of the proximal aperture of the stent within the candidate vein.

9. The method of claim 1 wherein after the fastening step the distal aperture of the stent attached to the candidate artery is configured into an ovoid or imperfectly circular shape.

10. The method of claim 1 wherein the candidate vein is a cephalic vein and the candidate artery is a radial artery.

11. The method claim 1 wherein the stent and vein structure is at least partially shaped by inserting and inflating a balloon inserted into the stent.

12. The method claim 1 further comprising: forming a desired anastomosis angle by inserting a conical shape tool into the stent distal aperture.

* * * * *